US012765916B2

(12) United States Patent
Wales

(10) Patent No.: US 12,765,916 B2
(45) Date of Patent: *Oct. 20, 2026

(54) MEDICAL DEVICE HAVING A ROTATABLE WORKING CHANNEL AND RELATED METHODS OF USE

(71) Applicant: Boston Scientific Scimed, Inc., Maple Grove, MN (US)

(72) Inventor: Ryan Wales, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 7 days.

This patent is subject to a terminal disclaimer.

(21) Appl. No.: 18/965,012

(22) Filed: Dec. 2, 2024

(65) Prior Publication Data

US 2025/0090198 A1 Mar. 20, 2025

Related U.S. Application Data

(63) Continuation of application No. 18/476,780, filed on Sep. 28, 2023, now Pat. No. 12,185,976, which is a continuation of application No. 17/445,283, filed on Aug. 17, 2021, now Pat. No. 11,806,044.

(60) Provisional application No. 63/073,952, filed on Sep. 3, 2020.

(51) Int. Cl.
*A61B 17/34* (2006.01)
*A61B 17/00* (2006.01)

(52) U.S. Cl.
CPC .............................. *A61B 17/3423* (2013.01); *A61B 2017/00389* (2013.01); *A61B 2017/3419* (2013.01); *A61B 2017/3445* (2013.01); *A61B 2217/005* (2013.01); *A61B 2217/007* (2013.01)

(58) Field of Classification Search
CPC ........................ A61B 1/00137; A61B 17/3423
See application file for complete search history.

(56) References Cited

U.S. PATENT DOCUMENTS

| | | | | |
|---|---|---|---|---|
| 7,371,211 B2 * | 5/2008 | Akiba | .............. | A61B 17/06066 600/156 |
| 9,549,661 B2 * | 1/2017 | Raybin | .............. | A61B 1/00066 |
| 2013/0242017 A1 | 9/2013 | Wada et al. | | |

(Continued)

FOREIGN PATENT DOCUMENTS

| | | |
|---|---|---|
| JP | H0636603 U | 5/1994 |
| JP | 2003210399 A | 7/2003 |

(Continued)

OTHER PUBLICATIONS

International Search Report and Written Opinion issued in International Application PCT/US2021/071214 on Dec. 23, 2021 (12 pages).

*Primary Examiner* — Si Ming Ku
(74) *Attorney, Agent, or Firm* — Bookoff McAndrews, PLLC

(57) ABSTRACT

A medical device comprising a shaft, a handle housing a proximal end of the shaft, a first channel extending throughout a lumen of the shaft, wherein the first channel is rotatable about a longitudinal axis of the shaft, the channel including a proximal end and a distal end, and an actuator, wherein a distal end of the actuator is configured to engage and disengage with the proximal end of the first channel, such that in an engaged position the actuator and the first channel are rotatable.

20 Claims, 5 Drawing Sheets

(56) References Cited

U.S. PATENT DOCUMENTS

| | | | |
|---|---|---|---|
| 2013/0242071 | A1 | 9/2013 | Wada et al. |
| 2014/0243594 | A1 | 8/2014 | Raybin et al. |
| 2019/0142400 | A1 | 5/2019 | Washburn et al. |
| 2019/0380562 | A1 | 12/2019 | Deuel et al. |

FOREIGN PATENT DOCUMENTS

| | | | |
|---|---|---|---|
| JP | 7138573 | B2 | 9/2022 |
| WO | 2012111761 | A1 | 8/2012 |
| WO | 2017211686 | A1 | 12/2017 |

* cited by examiner

MEDICAL DEVICE HAVING A ROTATABLE WORKING CHANNEL AND RELATED METHODS OF USE

CROSS-REFERENCE TO RELATED APPLICATIONS

This application is a continuation of U.S. application Ser. No. 18/476,780, filed on Sep. 28, 2023, which is a continuation of U.S. application Ser. No. 17/445,283, filed on Aug. 17, 2021, which claims the benefit of priority from U.S. Provisional Application No. 63/073,952, filed on Sep. 3, 2020, which is incorporated by reference herein in its entirety.

TECHNICAL FIELD

This disclosure relates generally to a medical device including a working channel that is rotatable, relative to the handle and the shaft of the medical device. At least some embodiments of the disclosure relate to a medical device having a working channel contained within a lumen of a medical device shaft.

BACKGROUND

In certain medical procedures, physicians and/or technicians need to control medical accessory devices that extend through the working channel of an endoscope. Such control may include the rotation of accessory devices within the working channel of the medical device. Physicians, at times, have difficulty rotating accessory devices extending through a fixed working channel due to the frictional forces between the device and the channel. In an attempt to overcome said frictional forces, physicians may apply an excessive rotational force onto the accessory device. This may cause a build-up of torque and tension between the accessory device and the working channel, and result in 1) damaging the accessory device, or 2) whipping the accessory device such that the distal end of said device will over-rotate relative to the desired degree of rotation. As a result, medical procedures may suffer from the above-discussed difficulties in controlling accessory devices.

SUMMARY OF THE DISCLOSURE

According to an example, a medical device may comprise a shaft, a handle housing a proximal end of the shaft, a first channel extending throughout a lumen of the shaft, wherein the first channel is rotatable about a longitudinal axis of the shaft, the channel including a proximal end and a distal end, and an actuator, wherein a distal end of the actuator is configured to engage and disengage with the proximal end of the first channel, such that in an engaged position the actuator and the first channel are rotatable. The actuator may comprise an elongated body that includes a lumen extending therethrough from a proximal end to a distal end of the elongated body.

In another example, the medical device may further comprise an actuator channel in fluid communication with the lumen of the shaft, wherein the actuator channel extends along an axis that is transverse to the longitudinal axis of the shaft, and the actuator channel sheaths at least a portion of the elongated body. The actuator may be configured to translate along a longitudinal axis of the actuator channel to engage and disengage the proximal end of the first channel, and the actuator is configured to rotate about a longitudinal axis of the actuator channel. The actuator is biased away from engagement with the proximal end of the first channel. The actuator may be spring-biased.

In another example, the medical device may further comprise a spring coiling around a portion of the elongated body that extends proximally outside of the actuator channel, wherein the spring is positioned between a distal surface of a knob and a proximal surface of the actuator channel.

In another example, the distal end of the actuator may include a first plurality of teeth protruding distally, wherein each of the first plurality of teeth is separated from one another by gaps along a circumference of the distal end of the actuator, and wherein the proximal end of the first channel includes a second plurality of teeth protruding proximally, wherein each of the second plurality of teeth is separated from one another by gaps along a circumference of the proximal end of the first channel. Each of the first plurality of teeth of the actuator may be configured to fit in each of the gaps of the first channel, and each of the second plurality of teeth of the channel may be configured to fit in each of the gaps of the actuator, thereby engaging the distal end of the actuator with the proximal end of the first channel.

In another example, a distal end of the shaft may include a distal abutment configured to abut against the distal end of the first channel, thereby inhibiting further distal movement of the first channel past the distal abutment. A proximal portion of the shaft may include a proximal abutment configured to inhibit further proximal movement of the first channel past the proximal abutment.

In another example, a proximal opening of the first channel may comprise a ring configured to receive at least one accessory device, and seal the proximal opening of the channel from fluid. A distal portion of the channel may comprise a holder configured to hold a distal portion of at least one accessory device passing through the distal opening of the channel. The handle may include a knob having a disc shape. The first channel may be configured to provide suction and/or insufflation through the distal opening of the first channel.

According to another example, a medical device may comprise a shaft including a lumen, a handle housing a proximal portion of the shaft, wherein the handle includes an opening leading to an actuator channel in fluid communication with the lumen of the shaft, a first channel extending throughout a lumen of the shaft, wherein the channel is rotatable about a longitudinal axis of the shaft, the first channel includes a proximal end and a distal end, and an actuator, wherein a portion of the actuator is sheathed within the actuator channel, the actuator is configured to translate along a longitudinal axis of the actuator channel to engage the proximal end of the first channel, and a rotation of the actuator, while engaged to the proximal end of the first channel, causes a simultaneous rotation of the first channel. The actuator may comprise a knob and an elongated body, wherein the elongated body includes a lumen extending therethrough from a proximal end and a distal end of the elongated body, the knob is fixed to the proximal end of the elongated body, and the knob includes an opening that is in fluid communication with the lumen of the elongated body. The actuator may be biased away from engagement with the proximal end of the first channel. The medical may further comprise a spring coiling around a portion of the elongated body that extends proximally outside of the actuator channel, wherein the spring is positioned between a distal surface of the knob and a proximal surface of the actuator channel, thereby biasing the actuator away from the proximal end of the first channel.

According to an example, a method of rotating an accessory device housed within a medical device, wherein the medical device comprises a first channel extending throughout a lumen of a shaft, wherein the first channel is rotatable about a longitudinal axis of the shaft, and an actuator configured to engage and rotate the first channel, wherein the accessory device extends within the first channel, and the first channel grips a distal portion of the accessory device, may include inserting a distal end of a shaft of the medical device into a body of a subject, and after the insertion step, engaging the actuator with the channel, and rotating the actuator, thereby rotating both the channel and the accessory device relative to the shaft.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1:
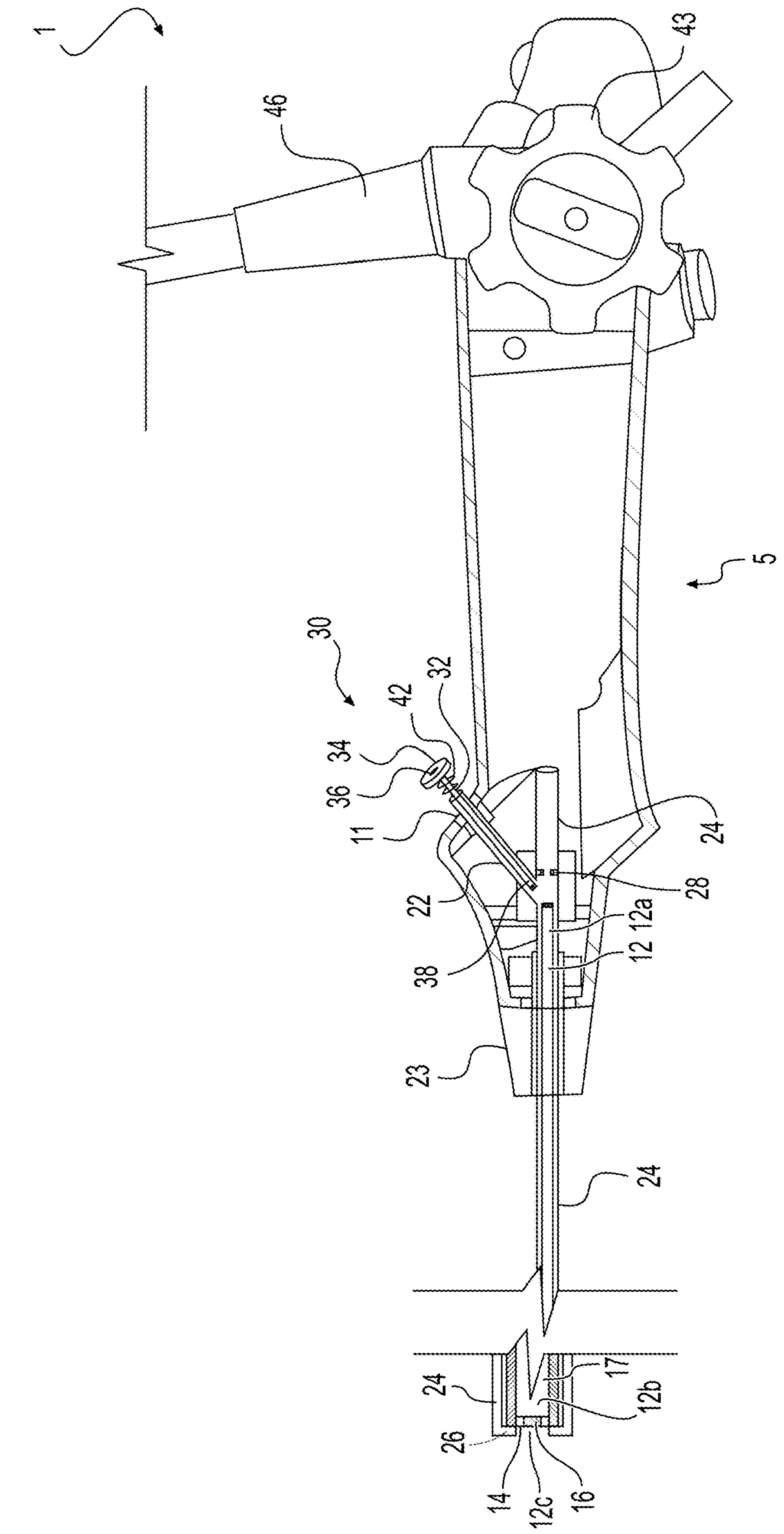
FIG. 1 is a partial cross-sectional view of a medical device, according to an embodiment.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., a patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately," are used to indicate a possible variation of +10% in a stated value or characteristic.

Embodiments of the disclosure may solve one or more of the limitations in the art. The scope of the disclosure, however, is defined by the attached claims and not the ability to solve a specific problem. The disclosure is drawn to a medical device including a working channel. The working channel may be rotatable clockwise or counter-clockwise by engagement with a port key, relative to a handle and a shaft of the medical device. The medical device can be, as an example, any scope (e.g., bronchoscope, duodenoscope, endoscope, colonoscope, ureteroscope, etc.), catheter, tool, instrument, or the like, having a shaft that extends distally from a handle. The working channel, likewise, may extend distally from a handle within a lumen of said shaft. In some embodiments, medical devices include a working channel that may be rotatable by engagement with a key extending through a lumen of a port on the medical device handle. Said key may be in one of two states—1) a default state, in which the key is not engaged with the working channel; and 2) an engaged state, in which the key is engaged with the working channel. The key may include a portion, e.g., a knob, that is outside of the port, and is accessible to a user. A user may interact with said portion (e.g., press, turn) to engage the port key with the working channel. The user may also rotate the key while in the engaged state, thereby simultaneously rotating the working channel.

The working channel is configured to receive at least one accessory device and to hold a distal portion of said accessory device via any suitable means (e.g., sphincter, collet). Thus, as the working channel is rotated, the accessory device rotates as well. Such a working channel eliminates the need for a user to manually rotate the accessory device by exerting rotational forces onto a proximal portion of said accessory device. Thus, said working channel minimizes the risks of damaging the accessory device, or causing the accessory device to whip. Further detail regarding the key, and the manner in which the key transitions between the aforementioned states are discussed below when referencing FIGS. 2A-2B, and 3A-3C.

Referring to FIG. 1, a medical device 1, e.g., a bronchoscope, according to an embodiment is shown. Medical device 1 includes a flexible shaft 24 (e.g., a catheter) and a handle 5 receiving a proximal portion of shaft 24. A proximal portion of shaft 24 may extend along a longitudinal axis of handle 5, and may be fixedly held within handle 5 by any suitable means. In some embodiments, a distal end of shaft 24 may include a distal abutment 26, which extends radially inward, toward the central axis of shaft 24. The degree by which distal abutment 26 extends radially inward is not particularly limited, so long as medical accessory devices are able to extend distally through a distal opening of shaft 24. In other embodiments, a proximal portion of shaft 24 may also include a proximal abutment 28, which also extends radially inward, toward the central axis of shaft 24. Distal abutment 26 and proximal abutment 28 (FIG. 3A) may serve the purpose of containing a working channel 12 (described in further detail below) within shaft 24. Abutments 26 and 28 may also limit the longitudinal mobility of channel 12 within shaft 24.

Medical device 1 further includes working channel 12 that extends throughout at least a portion of the lumen of shaft 24. Channel 12 includes a proximal end 12*a* and a distal end 12*b*. Proximal end 12*a* includes a proximal opening 15 (shown in FIG. 3B) leading to the opening of the lumen 17 of channel 12. Proximal end 12*a* is configured to be engaged by another component or means. For example, proximal end 12*a* may include a series of teeth protruding proximally (shown in greater detail in FIGS. 2A-2C), configured to engage and interlock with another series of teeth. However, proximal end 12*a* is not limited to including teeth, and may include any other suitable means configured for engagement. Distal end 12*b* includes a distal opening 12*c* in fluid communication with the lumen and proximal opening 15 of channel 12. Distal end 12*b* further includes a sphincter 14, or any other suitable means, configured to grip onto a distal portion of a medical accessory device extending through channel 12 and out of the distal opening. The manner in which sphincter 14 is coupled to distal end 12*b* is not particularly limited. For example, sphincter 14 may be securely fitted just proximal to distal opening 12*c* of distal end 12*b*, within lumen 17, by any suitable means, such as an adhesive. The material of sphincter 14 is not particularly limited, and, for example, may be a flexible, rubber material, e.g., silicon, BUNA-N. Furthermore, the structural shape of sphincter 14 is not particularly limited as well. For example, in some embodiments, sphincter 14 may be of an annular, ring like structure. In other embodiments, sphincter 14 may be an elastomeric slit valve. In some other embodiments, sphincter 14, may be in the shape of a pinhole, an o-ring, or may be a tapered portion of channel 12 including a flexible pinhole opening at the distal end. Sphincter 14 may include a central opening 16 configured to securely grip at least one accessory device extending therethrough. However, it is noted that distal end 12*b* is not limited to including sphincter 14, but may include any suitable means configured to hold or grip a distal portion of an accessory device extending out of the distal opening, e.g., a collet.

Channel 12 may be positioned within shaft 24, so that distal end 12*b* rests against distal abutment 26, and proximal end 12*a* is adjacently distal to the point at which a lumen 25 (shown in FIGS. 2A-2B) of channel 22 and the lumen of shaft 24 meet. In some embodiments, proximal end 12*a* may also be positioned distal to proximal abutment 28 on a proximal portion of shaft 24. Thus, in such embodiments, channel 12 may be contained between distal abutment 26 and proximal abutment 28. Channel 12 is fitted within the lumen of shaft 24 such that an outer surface of channel 12 may be flush against an inner surface of shaft 24, while allowing the rotation of channel 12 within the lumen of shaft 24. Alternatively, channel 12 is fitted within the lumen of shaft 24 to leave some annular space between the outer surface of channel 12 and the inner surface of shaft 24, to minimize friction forces during rotation. Channel 12 may be configured to receive accessory medical devices, and also provide suction or insufflation.

Handle 5, or some other device for actuating or controlling medical device 1 and any tools or devices associated with medical device 1, includes an actuating device 43. Actuating device 43 controls articulation of flexible shaft 24, and/or an articulation joint at a distal end of flexible shaft 24, in multiple directions. Device 43 may be, for example, a rotatable knob that rotates about its axis to push/pull actuating elements, e.g., steering wires (not shown). The actuating elements, such as cables or wires suitable for medical procedures (e.g., medical grade plastic or metal), extend distally from a proximal end of medical device 1 and connect to a distal portion of flexible shaft 24 to control movement thereof. Alternatively, or additionally, a user may operate actuating elements independently of handle 5. Distal ends of actuating elements may extend through flexible shaft 24 and terminate at an articulation joint and/or a distal tip of flexible shaft 24. For example, one or more actuating elements may be connected to an articulation joint, and actuation of actuating elements may control the articulation joint or the distal end of flexible shaft 24 to move in multiple directions (e.g. up/down and or left/right). In addition, one or more electrical cables (not shown) may extend from the proximal end of medical device 1 to the distal end of flexible shaft 24 and may provide electrical controls to imaging, lighting, and/or other electrical devices at the distal end of flexible shaft 24, and may transmit imaging signals from the distal end of flexible shaft 24 proximally to be processed and/or displayed on a display.

Handle 5 may also include ports 46, 11 for introducing and/or removing tools, fluids, or other materials from the patient. Port 46 may be connected to an umbilicus for introducing fluid, suction, insufflation, and/or wiring for electronic components. Port 11 may be used to introduce accessory devices. Port 11 receives a channel 22 that extends along an axis that is transverse to the longitudinal axis of shaft 24. The shape and length of channel 22 is not particularly limited. Channel 22 connects to shaft 24, so lumen 25 of channel 22 (shown in FIGS. 2A-2B) and the lumen of shaft 24 are in fluid communication with one another. Channel 22 is configured to house/sheath at least a portion of a port key 30.

Port key 30 includes a longitudinal body 32 and a knob 34. Body 32 may be a hollow, tubular body comprising a lumen 38 (shown in FIG. 2A) configured to receive a medical accessory device(s). The length of body 32 is not particularly limited, so long as a distal end of body 32 may engage with a proximal end 12*a* of a working channel 12 when body 32 is translated towards channel 12 (further discussed below). A distal end of body 32 may include a means for engaging proximal end 12*a* of channel 12. For example, the distal end of body 32 may include a series of teeth protruding distally (shown in greater detail in FIGS. 2A-2C), configured to engage and interlock with the series of teeth protruding from proximal end 12*a*. However, said distal end is not limited to including teeth, and may include any other suitable means configured for engagement with proximal end 12*a*. A proximal end of body 32 may be fixed or connected to knob 34. The manner in which body 32 is fixed/connected to knob 34 is not particularly limited. Knob 34 may be of a disc-shape, but is not limited thereto. Knob 34 may be of any suitable shape or design that allows for a user to turn or press knob 34, thereby rotating body 32 about or translating body 32 along the longitudinal axis of channel 22. Knob 34 comprises an opening 36, which is in fluid communication with the lumen of body 32. Opening 36 is configured to receive a medical accessory device(s), which may extend through both opening 36 and the lumen of body 32.

Figure 2A:
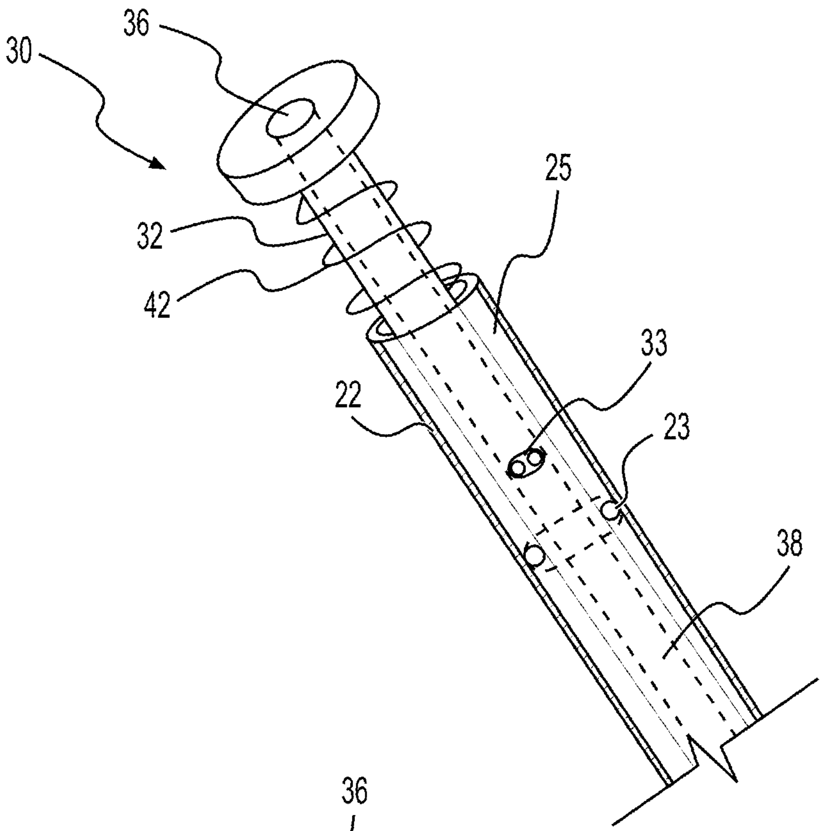
FIG. 2A is a partial cross-sectional view of a portion of the medical device of FIG. 1.

As shown in FIG. 2A, at least a portion of body 32 is sheathed within a lumen 25 of channel 22. An annular space may be defined between an outer surface of body 32 and an inner surface of channel 22. Alternatively, in other embodiments, body 32 may be flush against an inner surface of channel 22, while also being able to freely translate along or rotate about the longitudinal axis of channel 22. Furthermore, a spring 42 coils around the portion of body 32 that extends proximally outside of channel 22. Spring 42 is positioned between a distal surface of knob 34 and a proximal surface of channel 22, and the ends of spring 42 may be coupled to the aforementioned surfaces by any suitable means. Thus, due to the extension of spring 42, key 30 may be biased away from engagement with channel 12 by default. Also, by coupling spring 42 to the aforementioned surfaces, key 30 may be inhibited from falling out from the proximal opening of channel 22.

FIG. 2A further illustrates the presence of a channel O-ring 23 and a key O-ring 33. Both O-rings 23 and 33 are annular rings of any suitable material, preferably a flexible, rubber-like material, e.g., silicon, BUNA-N, etc. As shown, channel O-ring 23 is fitted around body 32 of key 30, in the annular space between an outer surface of body 32 and an inner surface of channel 22. The longitudinal placement of O-ring 23 with respect to body 32 is not particularly limited. O-ring 23 can be placed at any suitable longitudinal position about body 32. O-ring 33 may serve as a seal that inhibits foreign materials or fluids from entering and exiting channel 22. Key O-ring 33 may be fitted within lumen 38 of key 30. The longitudinal placement of O-ring 33 within lumen 38 is not particularly limited. O-ring 33 can be placed at any suitable longitudinal position within lumen 38. Given the annular shape of O-ring 33, accessory devices or instruments may be inserted through a central opening of O-ring 33. Moreover, O-ring 33 may serve as a seal that inhibits foreign materials or fluids from entering and exiting key 30 via lumen 38.

Figure 2B:
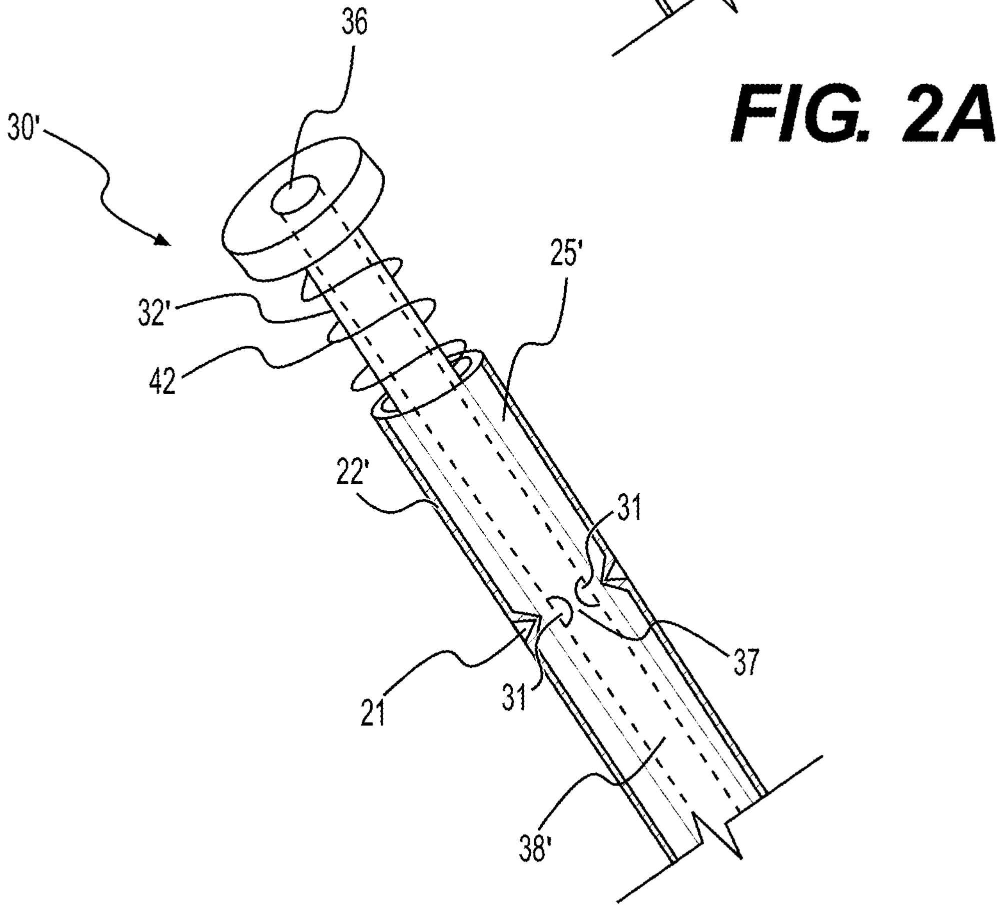
FIG. 2B is a partial cross-sectional view of a portion of a medical device according to another embodiment.

FIG. 2B illustrates an example of a different sealing means for channel 22' and key 30'. Channel 22' may be structured so that lumen 25' includes a tapered portion 21 between the proximal and distal ends of lumen 25'. Tapered portion 21 is tapered radially inwards until the inner surface of channel 22' contacts body 32', and is then tapered radially outward to the diameter of lumen 25' proximal and distal to the tapering. Tapered portion 21 effectively serves as a seal that inhibits foreign materials or fluids from entering and exiting channel 22'.

Similarly, key 30' may be structured so that lumen 38' tapers at tapered portion 31. Lumen 38' may be tapered so that a pinhole 37 remains in the center of tapered portion 31. Pinhole 37 allows for accessory devices or instruments to pass through lumen 38' via pinhole 37. The width or diameter of pinhole 37 is not particularly limited. For example, pinhole 37 may be of a similar diameter as the width of accessory devices or instruments. However, tapered portion 31 may be of a flexible material that allows for pinhole 37 to flex and receive devices or instruments of larger widths. Given the ability of pinhole 37 to stretch/flex, pinhole 37 may be of a smaller diameter and tapered portion 31 may effectively serve as a seal that inhibits foreign materials or fluids from entering and exiting key 30'.

As noted above, tapered portions 21, 31 are structural features of channel 22' and key 30'. To accommodate for tapered portions 21, 31 that are more flexible relative to the remaining structures of channel 22', and key 30', channel 22' and key 30' may be of a rubber like material, e.g., silicon, BUNA-N, of a higher durometer. Tapered portions 21, 31 may be of the same material, but of a lower durometer. This variance in durometer levels may be achieved by any suitable means. For example, tapered portions 21, 31 may be injection molded onto channel 22' and key 30', and the mold may be of the same materials (as channel 22', key 30') having lower durometers.

It is further noted that sealing means are not limited to the embodiments shown in FIGS. 2A and 2B. For example, device 1 may be without O-ring 23 or tapered portion 21 when body 32 may be flush against an inner surface of channel 22. Thus, various combinations and/or configurations of the above-described sealing means may be implemented.

Furthermore, medical device 1 may include a strain relief 23 that is attached to a distal end of handle 5. Strain relief 23 may be a cover of any suitable soft material that tapers distally and has an opening for shaft 24 at its distal end. Strain relief 23 is not particularly limited, and may assist in preventing shaft 24 from kinking.

Figure 3A:
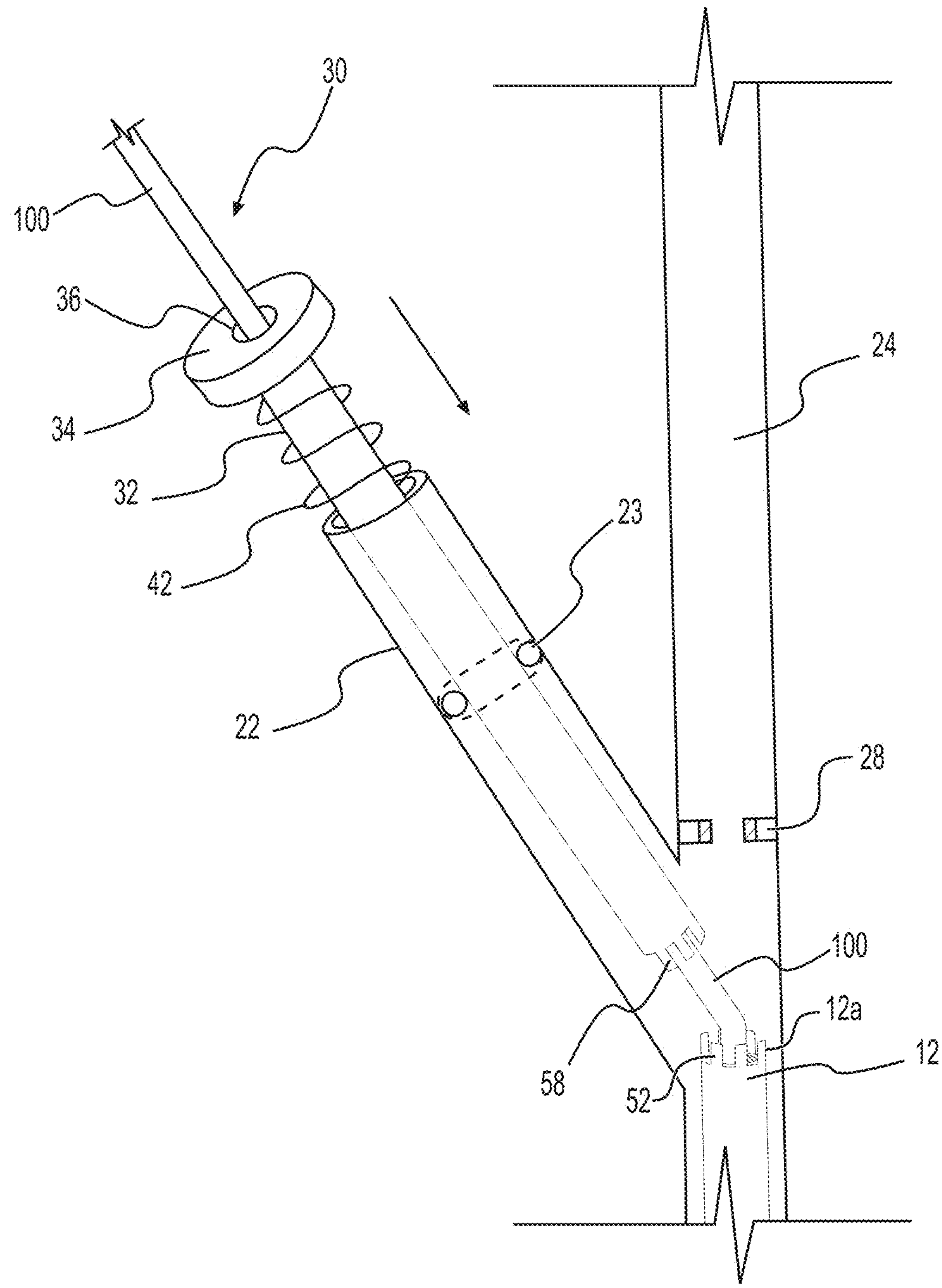
FIGS. 3A-3C are partial cross-sectional views of a portion of the medical device of FIG. 1.

FIG. 3A illustrates another view of key 30 in its default state. FIG. 3A shows the distal end of body 32 including a series of teeth 58 protruding distally, each tooth being separated from one another by an equal distance along a circumference of a distal tip of body 32. FIG. 3A also shows proximal end 12*a* including a series of teeth 52 protruding proximally, each tooth being separated from one another by an equal distance along a circumference of proximal end 12*a*. As indicated by the directional arrow, key 30 may translate along the longitudinal axis of channel 22, thereby transitioning from a default state to an engaged state. This may be done by pressing or pushing against knob 34 with a sufficient amount of force to compress spring 42, and driving key 30 towards proximal end 12*a* of working channel 12. The manner by which knob 34 is pressed or pushed against is not particularly limited. Although teeth 52, 58 are illustrated as a plurality of castellations, it is understood that teeth 52, 58 may be any protrusion/recess and corresponding reverse configuration such that the key 30 and channel 12 are selectively engageable and disengageable.

Figure 3B:
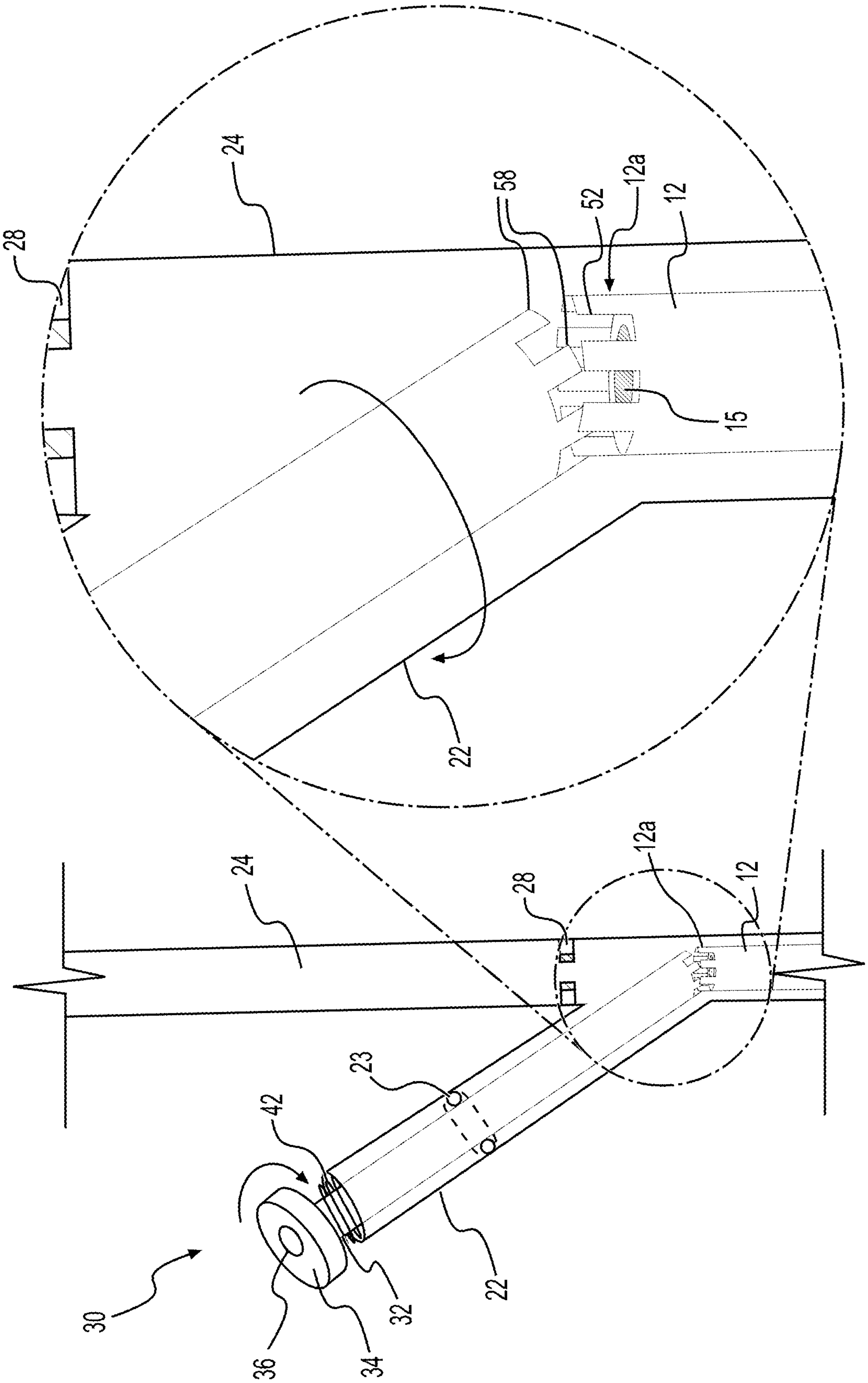

FIG. 3B illustrates a view of key 30 in its engaged state. In the engaged state, spring 42 is compressed and key 30 is advanced towards proximal end 12*a*. Teeth 58 of key 30 and teeth 52 of channel 12 are engaged and interlocked with one another such that that each of teeth 58 fill the separations or gaps between each of teeth 52. When engaged, knob 34 may be rotated about a longitudinal axis of channel 22 and body 32, as shown by a directional arrow, thereby rotating key 30 in the same direction, which in turn rotates working channel 12. It is noted that knob 34 may be rotated in either a clockwise or counter-clockwise direction, and is not limited to the direction in which the directional arrow points towards. The manner by which knob 34 is rotated is not particularly limited. As previously noted, distal end 12*b* further includes sphincter 14 (shown in FIG. 1*a*), or any other suitable means, configured to grip onto a distal portion of a medical accessory device extending out of the distal opening of channel 12. Thus, a medical accessory device inserted into opening 36, and extending through key 30 and channel 12, may be rotated (clockwise or counter-clockwise) simultaneously with channel 12.

Figure 3C:
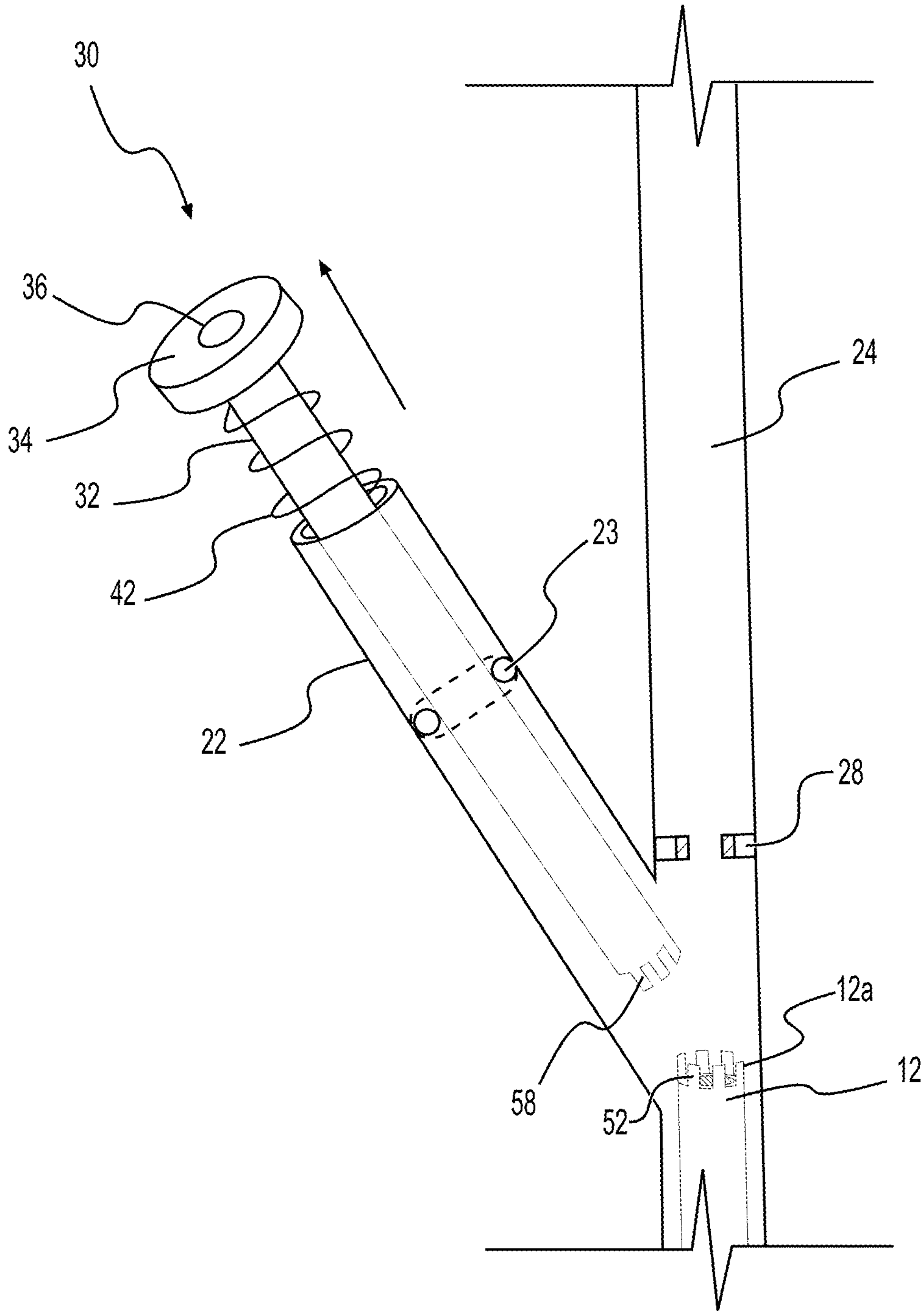

FIG. 3C illustrates a view of key 30 reverted back to its default state. Key 30 may revert to its default state when any force pressing or pushing against knob 34 is released, thereby allowing spring 42 to extend. This reversion is indicated by the directional arrow, and key 30 being in its original position, biased away from engagement with channel 12.

Referring to FIGS. 1A-3C, an example of how medical device 1 may be used is further discussed below. The distal end of shaft 24 of medical device 1 may be delivered into the body of a subject, adjacent to an intended target site. The delivery may be via a natural body orifice, such as the mouth, nose, anus, etc. Imaging associated with medical device 1, via any suitable image processing device, may assist in positioning of the distal end of shaft 24. A medical accessory device (not shown) may then be inserted into opening 36 of key 30. The accessory device may be advanced towards the distal end of shaft 24, past sphincter 14, which grips a distal portion of said accessory device. Depending on the position of the subject and/or the intended target site relative to medical device 1 and/or a user of medical device 1, the user may choose to rotate the accessory device relative to handle 5 and shaft 24. To rotate the accessory device, the user may first press against knob 34 of key 30 with a sufficient amount of force to compress spring 42, and advance key 30 towards working channel 12. Key 30 may be advanced until the distal end of key 30 and proximal end 12*a* of channel 12 are engaged. While engaged, the user may then turn knob 34 in a clockwise or counter-clockwise direction to rotate key 30, which causes the rotation of channel 12 in the same direction. The rotation of channel 12 causes a simultaneous rotation of the medical accessory device, which is gripped by channel 12 via sphincter 14. Thus, the user may rotate the medical accessory device to any desired degree, via the rotation of knob 34. After rotating the accessory device to the desired degree, the user may release any force applied to knob 34 to allow spring 42 to de-compress, and to revert key 30 to its default position, biased away from channel 12.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:

a shaft;

a handle housing a proximal end of the shaft;

a first channel extending throughout a first lumen of the shaft, the first channel including a proximal end; and an actuator including a distal end;

wherein the medical device includes an engaged state and an disengaged state, wherein, in the disengaged state, the distal end of the actuator and the proximal end of the first channel have a gap therebetween, wherein, in the engaged state, the distal end of the actuator contacts the proximal end of the first channel such that the first channel is rotatable with the actuator.

2. The medical device of claim 1, further comprising: a biasing element, wherein the biasing element is configured to automatically transition the medical device from the engaged state to the disengaged state.

3. The medical device of claim 2, wherein the actuator includes a knob, the knob including a distally facing surface, wherein a proximal end of the biasing element is biased against the distally facing surface of the knob.

4. The medical device of claim 1, wherein the medical device is configured to receive an accessory device, wherein the actuator includes an actuator lumen configured to receive the accessory device extended therethrough, wherein the first channel includes a channel lumen configured to receive the accessory device extended therethrough.

5. The medical device of claim 4, wherein, in the disengaged state and the engaged state, one or more of the actuator lumen and the channel lumen are configured to receive the accessory device.

6. The medical device of claim 4, wherein, in the disengaged state and in a configuration in which the accessory device is received by the channel lumen, the accessory device extends through the gap between the actuator and the first channel.

7. The medical device of claim 4, wherein the first channel includes a distal end, wherein the first channel includes a sphincter coupled to and positioned within the first channel, wherein the sphincter is configured to grip an outer surface of the accessory device such that the accessory device is rotatable with the first channel.

8. The medical device of claim 7, wherein, in the engaged state, rotation of the actuator rotates the first channel and a portion of the accessory device about a central longitudinal axis of the first channel.

9. The medical device of claim 8, wherein, in the engaged state, rotation of the actuator rotates the actuator about a central longitudinal axis of the actuator, wherein the central longitudinal axis of the actuator is angularly disposed relative to the central longitudinal axis of the first channel.

10. The medical device of claim 9, wherein the actuator includes a seal within the actuator lumen, wherein the seal is configured to grip an outer surface of the accessory device such that the accessory device rotates with the actuator.

11. A medical device, comprising:

a shaft;

a handle housing a proximal end of the shaft;

a first channel extending throughout a first lumen of the shaft, the first channel including a proximal end and a longitudinal axis; and an actuator including a distal end and a longitudinal axis;

wherein the medical device includes an engaged state and an disengaged state, wherein, in the engaged state, rotation of the actuator about the longitudinal axis of the actuator rotates the first channel about the longitudinal axis of the first channel, wherein the medical device is transitioned from the disengaged state to the engaged state by translation of the actuator along the longitudinal axis of the actuator toward the first channel.

12. The medical device of claim 11, wherein, in the disengaged state, the distal end of the actuator and the proximal end of the first channel have a gap therebetween.

13. The medical device of claim 11, wherein the longitudinal axis of the actuator is angularly disposed relative to the longitudinal axis of the first channel.

14. The medical device of claim 11, in the engaged state, the distal end of the actuator contacts the proximal end of the first channel.

15. The medical device of claim 11, further comprising: a biasing element configured to automatically transition the medical device from the engaged state to the disengaged state.

16. The medical device of claim 11, wherein the first channel includes a sphincter configured to grip an outer surface of an accessory device extending through an opening of the sphincter so that the accessory device rotates with the first channel.

17. The medical device of claim 11, wherein the medical device is configured to receive an accessory device such that, in the engaged state, the accessory device extends through a lumen of the actuator, a lumen of the first channel, and an opening of a sphincter disposed within the lumen of the first channel.

18. The medical device of claim 17, wherein, in the engaged state, rotation of the actuator causes a proximal portion of the accessory device to rotate about the longitudinal axis of the actuator and distal portion of the accessory device to rotate about the longitudinal axis of the first channel.

19. The medical device of claim 11, wherein a lumen of the actuator includes a seal configured to grip an accessory device extended therethrough.

20. A medical device, comprising:

a shaft;

a handle housing a proximal end of the shaft;

a first channel extending throughout a first lumen of the shaft, wherein the first channel is rotatable about a longitudinal axis of the shaft, the first channel including a proximal end and a distal end; and an actuator, wherein a distal end of the actuator is configured to selectively engage and disengage with the proximal end of the first channel, such that in an engaged position the actuator and the first channel are rotatable.

* * * * *